United States Patent [19]
Takahashi et al.

[11] Patent Number: 5,817,116
[45] Date of Patent: Oct. 6, 1998

[54] DETACHING TOOL FOR A TUBE FOR MEDICAL TREATMENT

[75] Inventors: Hiroshi Takahashi; Tokuharu Hayashi, both of Yokohama, Japan

[73] Assignee: Piolax Inc., Japan

[21] Appl. No.: 828,794

[22] Filed: Mar. 27, 1997

[30] Foreign Application Priority Data

Apr. 1, 1996 [JP] Japan .................................. 8-101918

[51] Int. Cl.⁶ .............................................. A61B 17/125
[52] U.S. Cl. ........................ 606/167; 606/120; 606/157; 30/124
[58] Field of Search .................... 606/120, 151, 606/157, 158, 167; 30/124

[56] References Cited

U.S. PATENT DOCUMENTS 4,588,160  5/1986  Flynn et al. ............................. 251/10
4,807,622  2/1989  Ohkaka et al. ......................... 606/167

FOREIGN PATENT DOCUMENTS 9308851  5/1993  WIPO .

*Primary Examiner*—Michael Powell Buiz
*Assistant Examiner*—David O. Reip
*Attorney, Agent, or Firm*—Ladas & Parry

[57] ABSTRACT

A detaching tool for a tube for medical treatment includes a body for gripping which has generally a U-shape and is resiliently deformable in an opening-closing direction in a bent portion. A separating member is separably disposed inside the body and the separating member generally forms a C-shape and is adapted to be pressed and closed by the body for gripping when the body for gripping is closed. A tube inserting portion is formed in the body and the separating member so that a tube for medical treatment may be inserted and held therein. First and second stream stopping portions are provided at a corresponding location inside the body and a corresponding location inside the separating member so as to press the pertinent portion of the tube and stop a stream inside the tube when the body is closed. First and second holding portions are provided on the body and the separating member so as to maintain the stream stopping states of the first and second stream stopping portions when the body is closed. A cutter for cutting the tube upon closing of the body is provided between the first and second stream stopping portions. A stopper is provided for preventing the cutter from arriving at the tube for a gripping force of a predetermined value or less.

10 Claims, 9 Drawing Sheets

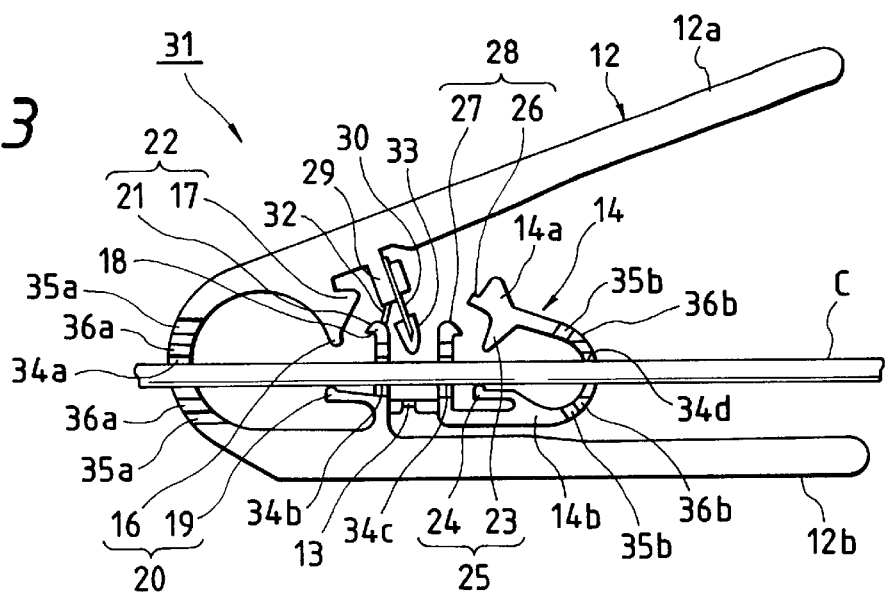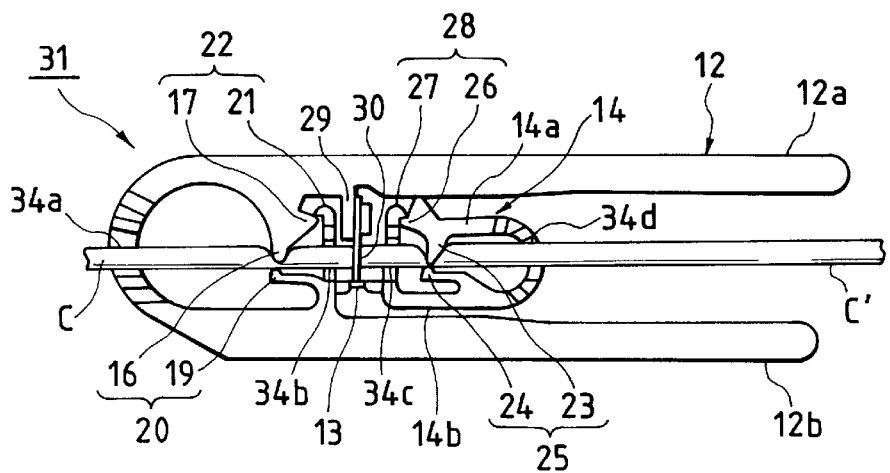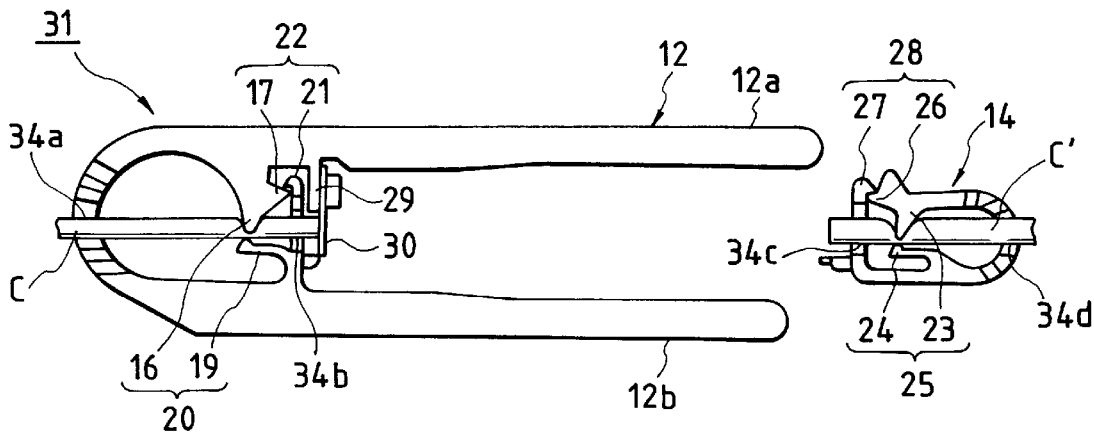

DETACHING TOOL FOR A TUBE FOR MEDICAL TREATMENT

BACKGROUND OF THE INVENTION

1. Field of the Invention

This invention relates to a detaching tool for a tube for medical treatment which is adapted to be attached to a tube for medical treatment used, for example, for artificial dialysis, intravenous drip or the like, and for a patient to detach the tube for medical treatment connected to his or her body upon occurrence of a calamity such as an earthquake or a fire while keeping stop the flow so that blood or the like may not flow out and to be able to take shelter quickly.

2. Related Background Art

For example, a kidney trouble patient must undergo medical treatment of artificial dialysis for five to eight hours once three days to purify a toxin in his or her blood. For this purpose, as shown in FIG. 12 of the accompanying drawings, the patient's body A and an artificial kidney device B are connected together by a tube C for medical treatment, whereby the blood circuit is closed. At this time, the connected end portions C' and C' of the tube C are attached to the patient's arms so as not to come off and therefore, the patient cannot move freely while lying down.

Accordingly, it in such a case, a calamity such as an earthquake or a fire occurs, the patient cannot escape by oneself and therefore, as shown in FIG. 13 of the accompanying drawings, a nurse or the like had to hold a tube C for flow path by clips D and D' to thereby block the blood stream, and sever the tube C between the clips D and D' by a pair of scissors E to thereby enable the patient to escape while keeping the connected end portions C' and C' attached to his or her arms.

In order to solve such a problem, the assignee of this application proposed a detaching tool for a tube for medical treatment as shown in FIGS. 9 and 10 of the accompanying drawings in Japanese Patent Laid-open Application No. 62-275470.

This detaching tool 11 is provided with a U-shaped body 12 for gripping comprising a pair of grip portions 12a and 12b connected together by a bent portion 12c, and a separating member 14 connected to the inside of the body 12 for gripping through a thin piece 13. The body 12 for gripping and the separating member 14 are ford with insertion holes 15a, 15b, 15c and 15d for inserting a medical fluid tube C thereinto.

A projection 16 is formed on the inner side of one grip portion 12a, and a pawl portion 17 is formed on a side of this projection 16. A protruded piece 18 is formed on the inner side of the other grip portion 12b, and a projection 19 extending at a right angle is formed on a side of this protruded piece 18. When the body 12 for gripping is closed, the projection 16 of the grip portion 12a is adapted to be urged against the projection 19 of the grip portion 12b to thereby hold and press the tube C and stop a blood stream, and these projections 16 and 19 together constitute a first stream stopping portion 20.

Also, a pawl portion 21 is formed on the tip end of the protruded piece 18. When the body 12 for gripping is closed, the pawl portion 17 of the grip portion 12a is adapted to come into engagement with the pawl portion 21 of the grip portion 12b to thereby maintain the body 12 for gripping in its closed state, i.e., a state in which the blood stream is stopped by the first stream stopping portion 20, and those pawl portions 17 and 21 together constitute a first holding portion 22.

The separating member 14 generally forms a C-shape, and one end portion 14a and the other end portion 14b thereof are adapted to be pressed and closed by the grip portions 12a and 12b when the grip portions 12a and 12b of the body 12 for gripping are closed.

A projection 23 is formed on the inner side of one and portion 14a of the separating member 14, and a projection 24 is formed on the inner side of the other end portion 14b thereof, and when the body 12 for gripping is closed and the separating member 14 is also closed, the tube C is adapted to be pressed by and between the projections 23 and 24 to thereby stop the blood stream, and these projections 23 and 24 together constitute a second stream stopping portion 25.

Further, a pawl portion 26 is formed on the tip end of one end portion 14a of the separating member 14, and the tip end of the other end portion 14b thereof is extended so as to be proximate to said one end portion 14a, and a pawl portion 27 is formed there. When the body 12 for gripping is closed and the separating member 14 is also closed, the pawl portions 26 and 27 are adapted to be engaged with each other to thereby maintain the separating member 14 in its closed state, i.e., a state in which the blood stream is stopped by the second stream stopping portion 25, and these pawl portions 26 and 27 together constitute a second holding portion 28.

Furthermore, a cutter 30 is mounted on the inner side of one grip portion 12a of the body 12 for gripping through a support piece 29. This cutter 30 is adapted to cut the tube C between the first stream stopping portion 20 and the second stream stopping portion 25 and to cut the thin piece 13 connecting the body 12 for gripping and the separating member 14 together.

Thus, according to this detaching tool 11, as shown in FIG. 9, the tube C for medical treatment is inserted into the insertion holes 15a, 15b, 15c and 15d and the detaching tool 11 is attached to the tube C for medical treatment. The attachment position of this detaching tool 11 is places near the patient's body, for example, F and F' or the like in FIG. 12.

When a calamity such as an earthquake or a fire occurs, the patient grips the grip portions 12a and 12b of the body 12 for gripping by his or her hands, as shown in FIG. 10. As a result of this, the tube C is pressed by and between the projections 16 and 19 of the first stream stopping portion 20 provided on the body 12 for gripping and the blood stream in that portion is stopped, and this state is maintained with the pawl portions 17 and 21 of the first holding portion 22 engaged with each other.

Also, the tube C is pressed by and between the projections 23 and 24 of the second stream stopping portion 25 provided on the separating member 14 and the blood stream in that portion is stopped, and this state is maintained with the pawl portions 26 and 27 of the second holding portion 28 engaged with each other.

Further, the cutter 30 cuts the tube C, and further cuts the thin piece 13 to thereby separate the body 12 for gripping and the separating member 14 from each other.

Then, as shown in FIG. 11 of the accompanying drawings, a tube C' connected to the patient's body is maintained in a state in which the blood stream is stopped by the second stream stopping portion 25 of the separating member 14, and the tube C connected to the artificial kidney device or the like is maintained in a state in which the blood stream is stopped by the first stream stopping portion 20 of the body 12 for gripping. As a result, it becomes possible for the patient to escape while wearing the tube C' in which the blood stream has bean stopped by the separating member 14.

However, the prior-art detaching tool 11 for a tube for medical treatment shown in FIGS. 9, 10 and 11 has suffered from the following problems.

There has been the undesirable possibility that when as shown in FIG. 9, the tube C for medical treatment is inserted into the insertion holes 15a, 15b, 15c and 15d of the detaching tool 11 to thereby attach the detaching tool 11 to the tube C for medical treatment or the patient changes his or her posture with the detaching tool 11 attached to the tube C for medical treatment, the grip portions 12a and 12b of the body 12 for gripping are inadvertently closed and operated, that is, the tube C is pressed by the first stream stopping portion 20 and the second stream stopping portion 25 and the blood stream is stopped, and the tube C is cut by the cutter 30.

Also, there has been the problem that when the detaching tool 11 is to be attached to the tube C for medical treatment, the end portion of the tube C for medical treatment rust be first inserted into the insertion holes 15a, 15b, 15c and 15d and therefore, the mounting of the detaching tool onto the tube C for medical treatment is cumbersome and takes much time. There has also been the problem that before the tube C for medical treatment is connected to the artificial kidney device or the like and a dialysis circuit or the like is assembled, the detaching tool 11 must be mounted an the tube C for medical treatment and therefore, there is the possibility of the detaching tool 11 being operated when it is being handled.

SUMMARY OF THE INVENTION

Accordingly, it is a primary object of the present invention to provide a detaching tool for a tube for medical treatment which is adapted not to be inadvertently operated during the handling thereof so that the stoppage of a blood stream or the cutting of the tube for medical treatment may take place.

It is another object of the present invention to provide a detaching tool for a tube for medical treatment which is easy to mount on the tube for medical treatment and can be mounted on the tube for medical treatment after a dialysis circuit or the like is assembled.

In order to accomplish the above object, according to one aspect of the invention, there is provided a detaching tool for a tube for medical treatment which comprises:

a body for gripping which has generally a U-shape and is resiliently deformable in an opening-closing direction in a bent portion;

a separating member separably disposed inside said body for gripping, generally forming a C-shape and adapted to be pressed and closed by said body for gripping when said body for gripping is closed;

a tube inserting portion formed in said body for gripping and said separating member so that a tube for medical treatment may be inserted and held therein;

a first stream stopping portion and a second stream stopping portion provided at a corresponding location inside said body for gripping and a corresponding location inside said separating member so as to press the pertinent portion of said tube for medical treatment and stop a stream inside said tube when said body for gripping is closed;

a first holding portion and a second holding portion provided on said body for gripping and said separating member so as to maintain the stream stopping states of said first stream stopping portion and said second stream stopping portion when said body for gripping is closed;

a cutter for cutting said tube for medical treatment between said first stream stopping portion and said second stream stopping portion when said body for gripping is closed; and a stopper for preventing said cutter from arriving at said tube for a gripping force of a predetermined value or less.

According to a further aspect of the invention, in the detaching tool for a tube for medical treatment, said separating member is connected to said body for gripping through a thin connecting portion, and said connecting portion is adapted to be cut and separated by said cutter when said body for gripping is closed.

According to a further aspect of the invention, in the detaching tool for a tube for medical treatment, said separating member is removably fitted inside said body for gripping.

According to a further aspect of the invention, in the detaching tool for a tube for medical treatment, said stopper comprises a connecting piece connecting the pair of grip portions of said body for gripping together and preventing said grip portions from being closed, and adapted to be broken away when a gripping force exceeding a predetermined value acts thereon.

According to a further aspect of the invention, in the detaching tool for a tube for medical treatment, said stopper comprises a thin piece extending in a width direction of the cutting edge of the cutter and a thickness of said thin piece is smaller than a width thereof.

According to a further aspect of the invention, in the detaching tool for a tubs for medical treatment, said stopper comprises a member extending from said body for gripping or said separating member so as to intercept a route in which the cutting edge of said cutter arrives at said tube, and adapted to be cut by said cutter when a gripping force exceeding a predetermined value acts thereon.

According to a further aspect of the invention, in the detaching tool for a tube for medical treatment, said thin piece constituting said stopper extends to connect said body for gripping and said separating member together.

According to a further aspect of the invention, in the detaching tool for a tube for medical treatment, by an initial load when said body for gripping is opened, the cutting edge of said cutter is resiliently urged to contact with said thin piece constituting said stopper, with such a degree of force that does not cut said thin piece.

According to a further aspect of the invention, the detaching tool for a tube for medical treatment includes a support member adapted to be inserted into said body for gripping along an axial direction of the tube and to be engaged with said body for gripping, and wherein said support member has a rib for holding said separating member stably in a direction substantially perpendicular to the axial direction of the tube According to a further aspect of the invention, in the detaching tool for a tube for medical treatment, said stopper comprises a cover which is disposed between the cutting edge of the cutter and the tube and is attached to the cutter.

According to a further aspect of the invention, in the detaching tool for a tube for medical treatment, a protective cover is provided on the cutting edge of said cutter.

According to a further aspect of the invention, in the detaching tool for a tube for medical treatment, said tube inserting portion comprises an insertion groove formed in said body for gripping and said separating member so that said tube can be inserted thereinto from sideways thereof.

According to a further aspect of the invention, in the detaching tool for a tube for medical treatment, said insertion groove is of such a shape that an entrance portion thereof is narrow to such a degree that said tube for medical treatment can be pushed thereinto and an inner part thereof is wide to such a degree as not to deform said tube, and at least one side portion of said insertion groove is endowed with a spring property so as to be capable of resiliently opening and closing.

According to a further aspect of the invention, in the detaching tool for a tube for medical treatment, said insertion grooves are made open in the same side.

According to a further aspect of the invention, in the detaching tool for a tube for medical treatment, said cutter has a cutting edge made obliquely such that the cutting edge projects longer toward a direction of the opening of said insertion groove.

According to a further aspect of the invention, in the detaching tool for a tube for medical treatment, at least one of spacings of said first and second stream stopping portions is made such that said at least one spacing is smaller than an outer diameter of said tube and the internal flow path of the tube is not blockaded in a state in which no gripping force is applied to said body for gripping.

In case of the use of the detaching tool for a tube for medical treatment according to the present invention, the tube for medical treatment is inserted into the tube insertion portion of the body for gripping and the separating member to thereby mount the detaching tool at a predetermined location on the tube for medical treatment. If a patient grips and closes the body for gripping when a calamity such as an earthquake or a fire occurs, the separating member disposed inside thereof is also closed.

As a result, the first and second stream stopping portions provided inside the body for gripping and the separating member press the tube for medical treatment to stop the stream of blood or the like inside the tube. Also, the first and second holding portions provided on the body for gripping and the separating member maintain the body for gripping and the separating member in their closed state to thereby maintain the above-described stream stopping state. Simultaneously therewith, a cutter cuts the tube for medical treatment between the first stream stopping portion and the second stream stopping portion.

Design is made such that at that time, an end portion of the tube for medical treatment which is connected to the patient's body is held by the separating member and an end portion of the tube for medical treatment which is connected to an artificial kidney device is held by the body for gripping, whereby the patient can quickly take shelter while wearing the cut tube for medical treatment and the separating member which closes the cut tube.

In a detaching tool for a tube for medical treatment according to an aspect of the present invention, provision is made of a stopper for preventing said cutter from reaching said tube under a gripping force of a predetermined value or less, whereby the body for gripping can be prevented from being inadvertently closed and operated with the detaching tool mounted on the tube for medical treatment.

In a detaching tool for a tube for medical treatment according to a further aspect of the present invention, the separating member and the body For gripping are made integral with each other through a connecting portion and therefore, molding, assembling and handling become easy. Also, when the tube is cut by the cutter, the connecting portion is cut at the same time, whereby the separating member can be separated from the body for gripping by one touch.

In a detaching tool for a tube for medical treatment according to still a further aspect of the present invention, the body for gripping and the separating member are made discrete from each other, whereby even if the detaching tool is operated to detach the separating member from the body for gripping, it will become possible to reuse the separating member by fitting the separating member into the body for gripping.

In a detaching tool for a tube for medical treatment according to yet still a further aspect of the present invention, the pair of grip portions of the body for gripping are connected together by a stopper and therefore, during operation, it is difficult for the positional deviation between the pair of grip portions to occur, and it is possible to cause the cutter to reliably abut against a desired portion of the tube or the like to thereby reduce the occurrence of erroneous cutting.

In a detaching tool for a tube for medical treatment according to a further aspect of the present invention, since the thin piece constituting the stopper extends in the width direction of the cutting edge of the cutter with a thickness smaller than the width thereof, the function of the stopper is assured with less load required for breaking the stopper while enhancing stability the pair of grip portions of the body for gripping portions of the body for gripping in the lateral direction thereof.

In a detaching tool for a tube for medical treatment according to a further aspect of the present invention, the tube can be prevented from inadvertently touching the cutter before the detaching tool is operated, and the handling as during the insertion of the tube becomes easy. Also, the releasing of the stopper is performed not by breaking away, but by cutting and therefore, there can be provided structure excellent in shock resistances In a detaching tool for a tube for medical treatment according to still a further aspect of the present invention, the body for gripping and the separating member are connected together by a stopper and therefore, the separating member can be held more reliably.

In a detaching tool for a tube for medical treatment according to yet still a further aspect of the present invention, the cutting edge of the cutter is urged against and is in contact with a thin piece constituting the stopper in the initial state, whereby when gripping the body for gripping, the lateral vibration of the cutter can be prevented to thereby prevent the erroneous cutting of the tube. Also, when the stopper is connected to the separating member, the separating member can be pressed through the stopper and can be stably prevented from coming off the body for gripping.

In a detaching tool for a tube for medical treatment according to a further aspect of the present invention, the lateral vibration of the separating member can be prevented by the ribs of a support member and during the handling such as the setting of the tool to the tube, the separating member can be prevented from coming off the body for gripping.

In a detaching tool for a tube for medical treatment according to still a further aspect of the present invention, a protective cover is provided over the cutting edge of the cutter, whereby the tube or the like can be prevented from being damaged even if it lightly touches the cutter during handling.

In a detaching tool for a tube for medical treatment according to yet still a further aspect of the present invention, the tube can be inserted into an insertion groove from sideways of the body for gripping and the separating member and held therein and therefore, after the tube for medical treatment is connected to an artificial kidney device or the like to thereby assemble a dialysis circuit or the like, the detaching tool can be easily and quickly mounted at any location.

In a detaching tool for a tube for medical treatment according to a further aspect of the present invention, the insertion of the tube can be facilitated by a spring property provided to at least one side of the insertion groove and moreover, when the tube is inserted into the insertion groove, it can be made difficult by the narrowed entrance for the tube to be drawn out of the insertion groove.

In a detaching tool for a tube for medical treatment according to still a further aspect of the present invention, the insertion groove opens to the same side and therefore, the insertion of the tube becomes easier.

In a detaching tool for a tube for medical treatment according to still a further aspect of the present invention, when during an emergency, the body for gripping is gripped to operate the detaching tool, the tube pushed by the cutter is made easy to move toward the inner part of the insertion groove but difficult to move toward the opening of the insertion groove, to thereby prevent the tube from slipping out of the opening, and the cutting of the tube can be reliably done.

In a detaching tool for a tube for medical treatment according to yet still a further aspect of the present invention, when the tube is inserted into the insertion groove, the tube is pressed against and held in at least one of the first stream stopping portion and the second stream stopping portion to such a degree that the internal flow path is not blockaded and therefore, it becomes difficult for the tube to slip out.

In order to accomplish the above object, according to another aspect of the invention, there is provided a detaching tool for a tube for medical treatment which comprises:

a body for gripping which has generally a U-shape and is resiliently deformable in an opening-closing direction in a bent portion;

a separating member separably disposed inside said body for gripping, generally forming a C-shape and adapted to be pressed and closed by said body for gripping when said body for gripping is closed;

a tube inserting portion formed in said body for gripping and said separating member so that a tube for medical treatment may be inserted and held therein;

a first stream stopping portion and a second stream stopping portion provided at a corresponding location inside said body for gripping and a corresponding location inside said separating member so as to press the pertinent portion of said tube for medical treatment and stop a stream inside said tube when said body for gripping is closed;

a first holding portion and a second holding portion provided on said body for gripping and said separating member so as to maintain the stream stopping states of said first stream stopping portion and said second stream stopping portion when said body for gripping is closed; and a cutter for cutting said tube for medical treatment between said first stream stopping portion and said second stream stopping portion when said body for gripping is closed, wherein said tube inserting portion comprises insertion grooves formed in said body for gripping and said separating member so that said tube can be inserted thereinto from sideways thereof.

According to a further aspect of the inventions in the detaching tool for a tube for medical treatment, said insertion groove is of such a shape that an entrance portion thereof is narrow to such a degree that said tube for medical treatment can be pushed thereinto and an inner part thereof is wide to such a degree as not to deform said tube, and at least one side portion of said insertion groove is endowed with a spring property so as to be capable of resiliently opening and closing.

According to a further aspect of the invention, in the detaching tool for a tube for medical treatment, said insertion grooves are made open in the same side.

According to a further aspect of the invention, in the detaching tool for a tube for medical treatment, said cutter has a cutting edge made obliquely such that the cutting edge projects longer toward a direction of the opening of said insertion groove.

According to a further aspect of the invention, in the detaching tool for a tube for medical treatment, at least one of spacings of said first and second stream stopping portions is made such that said at least one spacing is smaller than an outer diameter of said tube and the internal flow path of the tube is not blockaded in a state in which no gripping force is applied to said body for gripping.

In a detaching tool for a tube for medical treatment according to a further aspect of the present invention, the tube can be inserted into an insertion groove from sideways of the body for gripping and the separating member and held therein and therefore, after the tube for medical treatment is connected to an artificial kidney device or the like to thereby assemble a dialysis circuit or the like, the detaching tool can be easily and quickly mounted at any location.

In a detaching tool for a tube for medical treatment according to a further aspect of the present invention, the insertion of the tube can be facilitated by a spring property provided to at least one side of the insertion groove and moreover, when the tube is inserted into the insertion groove, it can be made difficult by the narrowed entrance for the tube to be drawn out of the insertion groove.

In a detaching tool for a tube for medical treatment according to still a further aspect of the present invention, the insertion groove opens to the same side and therefore, the insertion of the tube becomes easier.

In a detaching tool for a tube for medical treatment according to still a further aspect of the present invention, when during an emergency, the body for gripping is gripped to operate the detaching tool, the tube pushed by the cutter is made easy to move toward the inner part of the insertion groove but difficult to move toward the opening of the insertion groove, to thereby prevent the tube from slipping out of the opening, and the cutting of the tube can be reliably done.

In a detaching tool for a tube for medical treatment according to yet still a further aspect of the present invention, when the tube is inserted into the insertion groove, the tube is pressed against and held in at least one of the first stream stopping portion and the second stream stopping portion to such a degree that the internal flow path is not blockaded and therefore, it becomes difficult for the tube to slip out.

BRIEF DESCRIPTION OF THE DRAWINGS

FIG. 3 is a side view showing the same detaching tool as it is attached to a tube for medical treatment.

FIG. 4 is a side view showing the body for gripping of the same detaching tool as it is closed.

FIG. 5 is a side view showing the separating member of the same detaching tool as it is separated.

DESCRIPTION OF THE PREFERRED EMBODIMENTS

Figure 1:
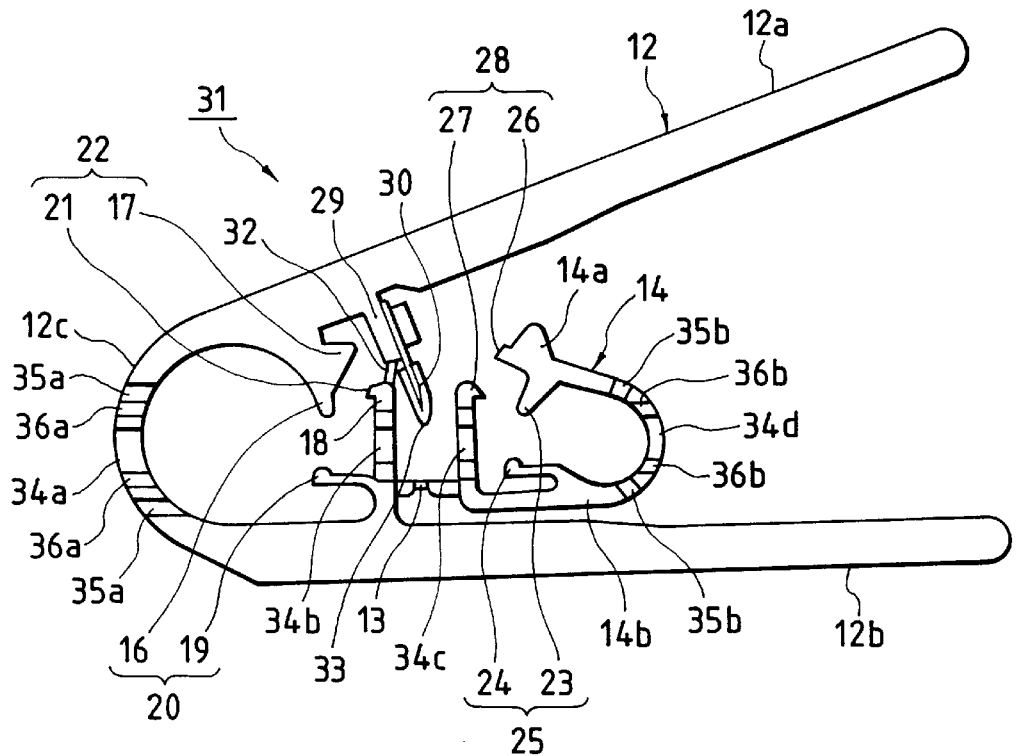
FIG. 1 is a side view showing an embodiment of a detaching tool for a tube for medical treatment according to the present invention.

In FIGS. 1, 2, 3, 4 and 5, there is shown an embodiment of a detaching tool for a tube for medical treatment according to the present invention. In these figures, the same portions as those of the detaching tool for a tube for medical treatment according to the prior art shown in FIGS. 9, 10 and 11 are given the same reference characters and need not be described.

As shown in FIG. 1, this detaching tool 31 for a tube for medical treatment is provided with a stopper 32 for preventing the grip portions 12a and 12b of a body 12 for gripping from being inadvertently closed. In the case of this embodiment, the stopper 32 comprises a thin piece connecting a supporting piece 29 for a cutter 30 provided on the inner side of one grip portion 12a and a portion on which the pawl portion 21 of the other grip portion 12b is provided (the tip end portion of a protruded piece 18) together. This thin piece may preferably be formed with a groove of V-shaped cross-sectional shape in the central portion thereof so as to be readily broken away when the body 12 for gripping is forcibly closed.

Also, a protective cover 33 formed of soft synthetic resin is mounted on the cutting edge portion of a cutter 30. This protective cover 33 serves to prevent a tube C for medical treatment from being injured when the cutter 30 inadvertently contacts with the tube C for medical treatment, but is made of a material which does not harper cutting when the cutter 30 is forcibly urged against the tube C for medical treatment to cut the latter. The protective cover 33 is preferably made of (1) a soft material, for example, resin or rubber covering the cutting edge of the cutter by dipping or the like, (2) a soft sheet, for example, a soft synthetic resin sheet, a tacky tape or a foamed urethane tape joined with one surface or both surfaces of the cutter so that a portion thereof may be extended from the cutting edge of the cutter, or (3) a foamed urethane block, a silicon tube or the like up to halfway of which the cutting edge of the cutter is inserted.

Figure 9:
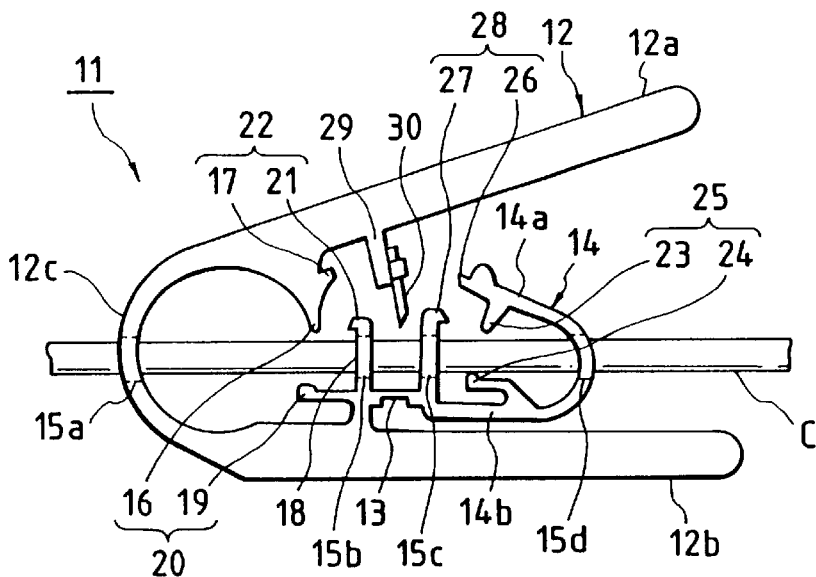
FIG. 9 is a side view showing an example of a detaching tool for a tube for medical treatment according to the prior art.
Figure 10:
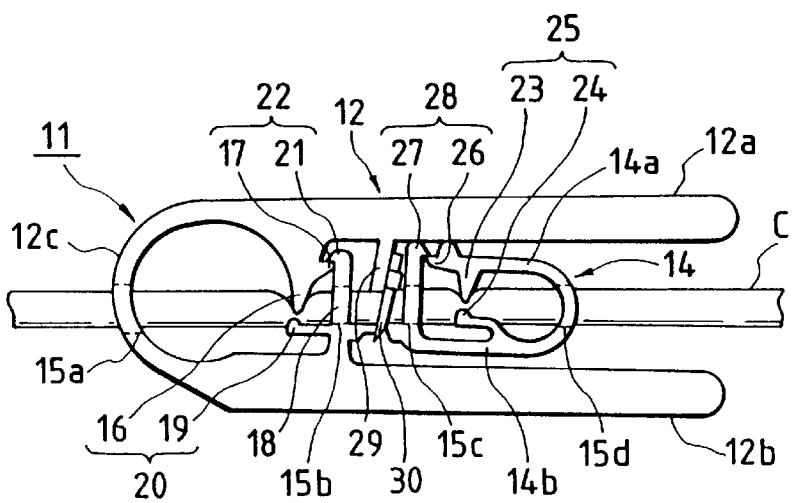
FIG. 10 is a side view showing the body for gripping of the same detaching tool as it is closed.
Figure 11:
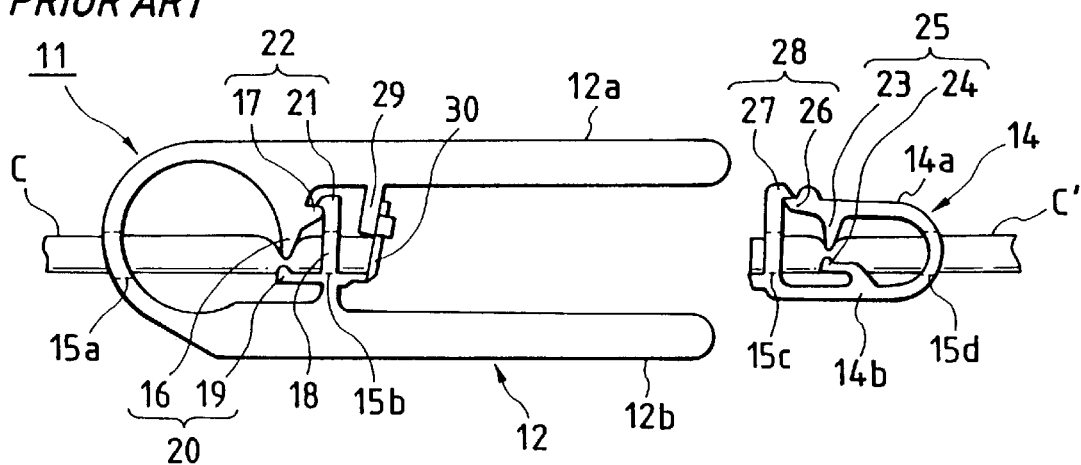
FIG. 11 is a side view showing the separating member of the same detaching tool as it is separated.
Figure 12:
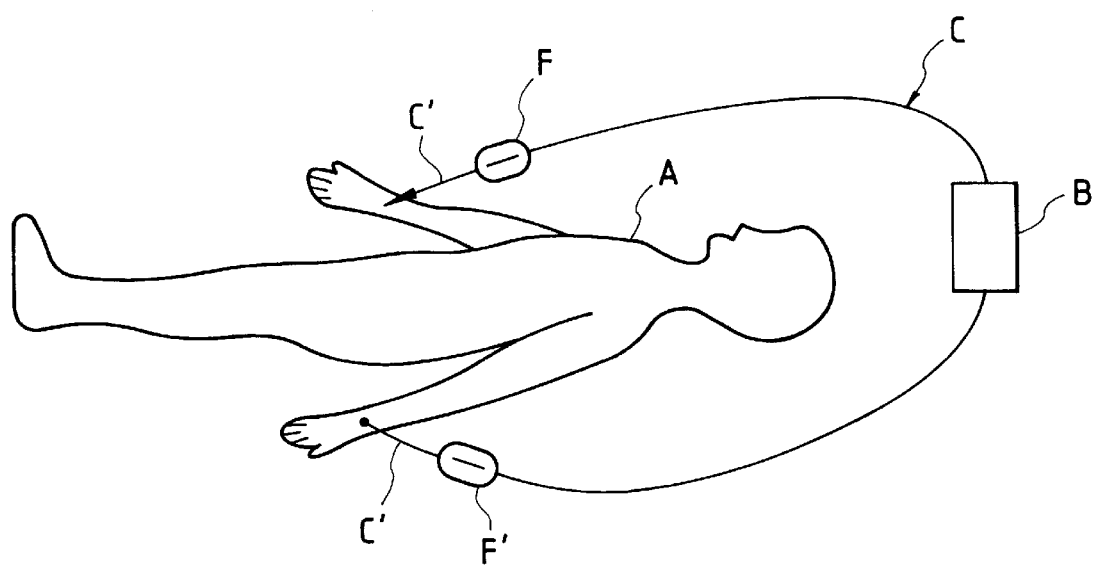
FIG. 12 is an illustration showing a method of artificial dialysis.
Figure 13:
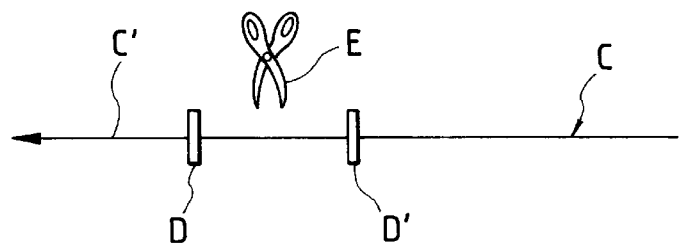
FIG. 13 is an illustration showing an example of a prior-art method of detaching a tube for medical treatment when a calamity or the like has occurred during artificial dialysis.

Further, in this detaching tool 31 for a tube for medical treatment, instead of the insertion holes 15a, 15b, 15c and 15d of the detaching tool shown in FIGS. 9, 10 and 11, insertion grooves 34a, 34b, 34c and 34d are formed at predetermined locations on the body 12 for gripping and the separating member 14. These insertion grooves 34a, 34b, 34c and 34d, as shown in FIG. 2, are of a shape in which the entrances thereof are narrow and the inner parts thereof are enlarged in diameter, and are designed such that when the tube C for medical treatment is compressed and pushed in through the entrances, it is widened and held in the inner part so as not to inadvertently slip out of the grooves.

Figure 2:
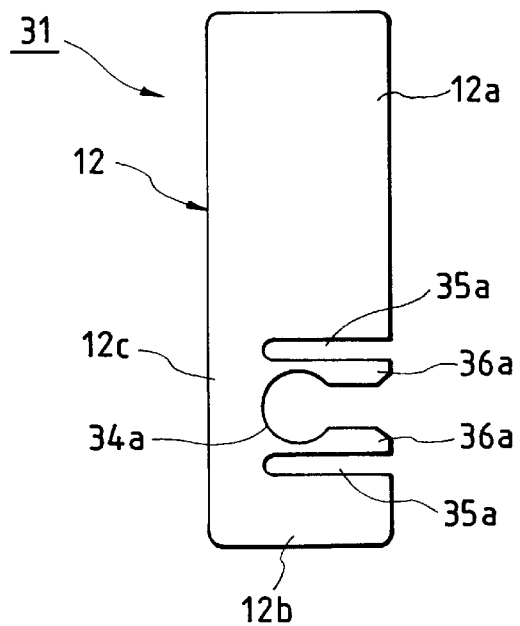
FIG. 2 is a front end view of the same detaching tool.

Also, in the insertion grooves 34a and 34d at the opposite ends, as shown in FIG. 2 (in FIG. 2, only the insertion groove 34a is shown, but the insertion groove 34d also is of the same structure as the insertion groove 34a), grooves 35a, 35a, 35b, 35b are formed on the opposite sides thereof, whereby there are formed independent opposite side portions 36a, 36a, 36b, 36b having a spring property, and by these opposite side portions 36a, 36a, 36b, 36b, the tube C for medical treatment can be easily inserted with the opposite side portions 36a, 36a, 36b, 36b resiliently widened.

Grooves 35a and 35b may be formed in the side portion of one of the insertion grooves 34a and 34d, and only the side portions 36a and 36b of one of the insertion grooves 34a and 34d may have a spring property.

In case of the use of this detaching tool 31, the tube C for medical treatment can be inserted from sideways into the insertion grooves 34a, 34b, 34c and 34d of the detaching tool 31 to thereby simply mount the detaching tool 31 at any position on the tube C for medical treatment by one touch. Also, it becomes possible to mount the detaching tool 31 after the tube C for medical treatment is connected to a patient's body or an artificial kidney device or the like to form a dialysis circuit or the like.

FIG. 3 shows the detaching tool 31 as it is mounted on the tube C for medical treatment, and in the present invention, there is provided a stopper 32 for preventing the grip portions 12a and 12b of the body 12 for gripping from being inadvertently closed and therefore, the body 12 for gripping can be prevented from being inadvertently closed and operating, that is, the tube C can be prevented from being pressed by a first stream stopping portion 20 and a second stream stopping portion 25 to thereby stop the blood stream and can be prevented from being cut by the cutter 30 while the detaching tool 31 is being handled or while the patient is subjected to artificial dialysis or the like. Also, the protective cover 33 is put on the cutting edge of the cutter 30 and therefore, as when the tube C for medical treatment is inserted into the insertion grooves 34a, 34b, 34c and 34d of the detaching tool 31, even if the tube C for medical treatment touches the cutter 30, the tube C for medical treatment will be prevented from being injured.

When a calamity such as an earthquake or a fire has occurred, the patient grips and closes the grip portions 12a and 12b of the body 12 for gripping, as shown in FIG. 4, whereby the tube C is pressed by and between the projections 16 and 19 of the first stream stopping portion 20 provided on the body 12 for gripping and the blood stream on that portion is stopped, and the pawl portions 17 and 21 of a first holding portion come into engagement with each other and that state is maintained.

Also, the tube C is pressed by and between the projections of the second stream stopping portion 25 provided on the separating member 14 and the blood stream in that portion is stopped, and the pawl portions 26 and 27 of a second holding portion 28 come into engagement with each other and that state is maintained Further, the cutter 30 breaks through the protective cover 33 put on the cutting edge thereof to thereby cut the tube C and cut the thin piece 13, thus separating the body 12 for gripping and the separating member 14 from each other Accordingly, as shown in FIG. 5, the body 12 for gripping connected to the tube C for medical treatment and the separating member 14 connected to a tube C for medical treatment can be separated from each other, and the tube C' for medical treatment is designed to be connected to the patient's body, whereby the patient can quickly take shelter while wearing the cut tube C' for medical treatment and the separating member 14 for closing it. Also, the tube C for medical treatment connected to the artificial kidney device or the like prevents the blood stream or the like from flowing out, by the body 12 for gripping.

Figure 6:
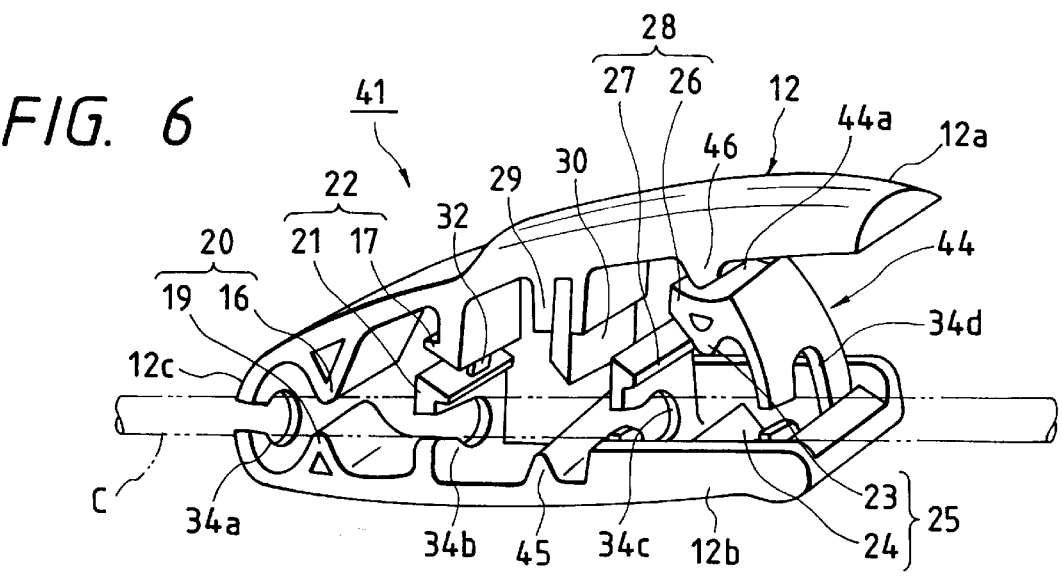
FIG. 6 is a perspective view showing another embodiment of the detaching tool for a tube for treatment according to the present invention.
Figure 7:
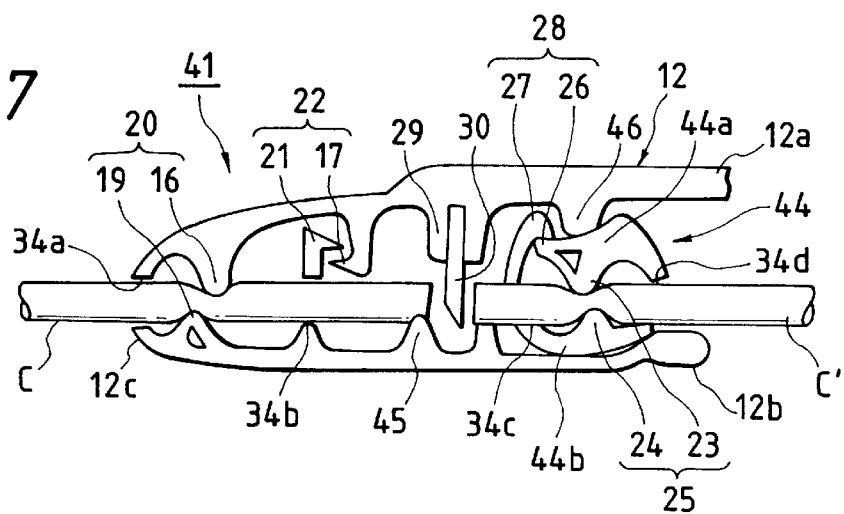
FIG. 7 is a side view showing the body for gripping of the same detaching tool as it is closed.
Figure 8:
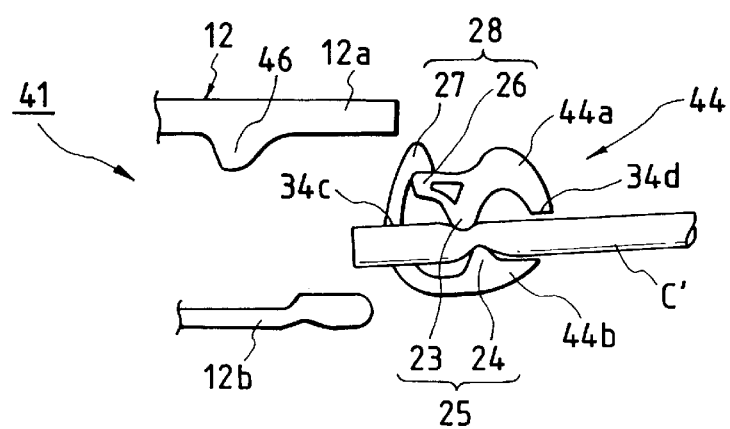
FIG. 8 is a side view showing the separating member of the same detaching tool as it is separated.

In FIGS. 6, 7 and 8, there is shown another embodiment of the detaching tool for a tube for medical treatment according to the present invention.

The detaching tool 41 of this embodiment is basically of the same structure as the aforedescribed embodiment shown in FIGS. 1, 2, 3, 4 and 5, but the main difference thereof from the aforedescribed embodiment is that a separating member 44 is formed discretely from the body 12 for gripping.

That is, the separating member 44 is generally of a rounded C-shaper and one end portion 44a thereof abuts against a projection 46 formed on the inner side of one grip portion 12a of the body 12 for gripping, and the other end portion 44b thereof abuts against the inner side of the other grip portion 12b of the body 12 for gripping, so that the separating member 44 is removably fitted in the inner side of the body 12 for gripping.

The tip end of one end portion 44a of the separating member 44 forms a pawl portion 26, and the tip end of the other end portion 44b thereof forms a pawl portion 27, and these pawl portions 26 and 27 together constitute a second holding portion 28 for maintaining the separating member 44 in its closed state. Also, a projection 23 formed on the inner side of one end portion 44a of the separating member 44 and a projection 24 formed on the inner side of the other end portion 44b thereof together constitute a second stream stopping portion 25.

On the other hand, the body 12 for gripping, as in the previous embodiment, is provided with a first stream stopping portion 20 comprising projections 16 and 19, and a first holding portion 22 comprising pawl portions 17 and 21. Also, correspondingly to the cutter 30 provided on one grip portion 12a, a projection 45 for receiving the tube C fop medical treatment is formed on the other grip portion 12b, and the tube C for medical treatment is easy to cut by the cutter 30.

In this detaching tool 41, when during a calamity such as an earthquake or a fire, the patient grips and closes the grip portions 12a and 12b of the body 12 for gripping, as shown in FIG. 7, the tube C for medical treatment is pressed by and between the projections 16 and 19 of the first stream stopping portion 20 of the body 12 for gripping and the projections 23 and 24 of the second stream stopping portion 25 of the separating member 44 and the flow path is closed, and the pawl portions 21 and 17 of the first holding portion 22 of the body 12 for gripping and the pawl portions 26 and 27 of the second holding portion 28 of the separating member 44 come into engagement with each other, whereby the above-described stream stopping state is maintained. Further, the tube C for medical treatment is cut by the cutter 30.

In this state, the patient can remove the separating member 44 from the body 12 for gripping, as shown in FIG. 8, and quickly take shelter while wearing the cut one tube C' for medical treatment and the separating member 44. Also, the other tube C for medical treatment left connected to the artificial kidney device or the like has its stream stopping state maintained by the first stream stopping portion 20 of the body 12 for gripping.

Figure 14:
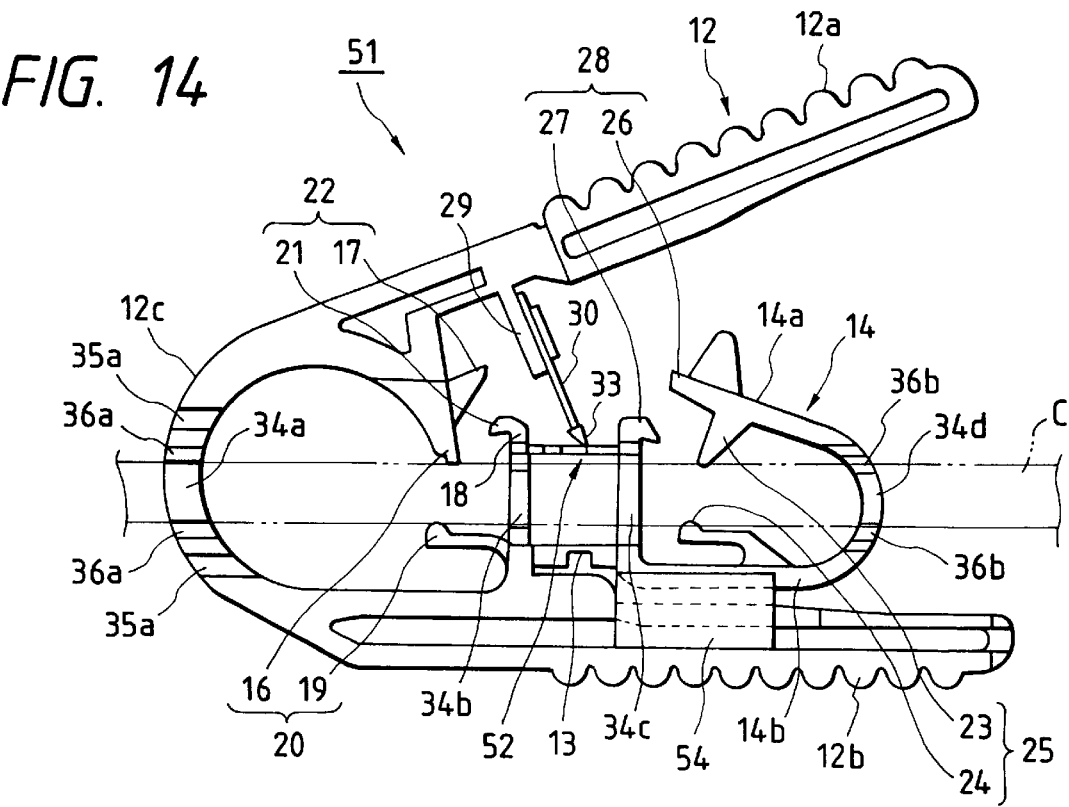
FIG. 14 is a side view showing the state of still another embodiment of the detaching tool for a tube for medical treatment according to the present invention before operated.
Figure 15:
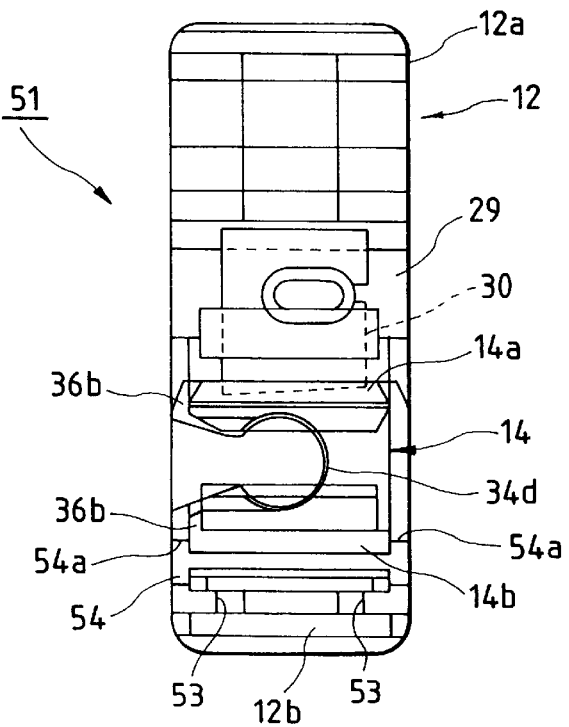
FIG. 15 is a rear end view of the same detaching tool.
Figure 16:
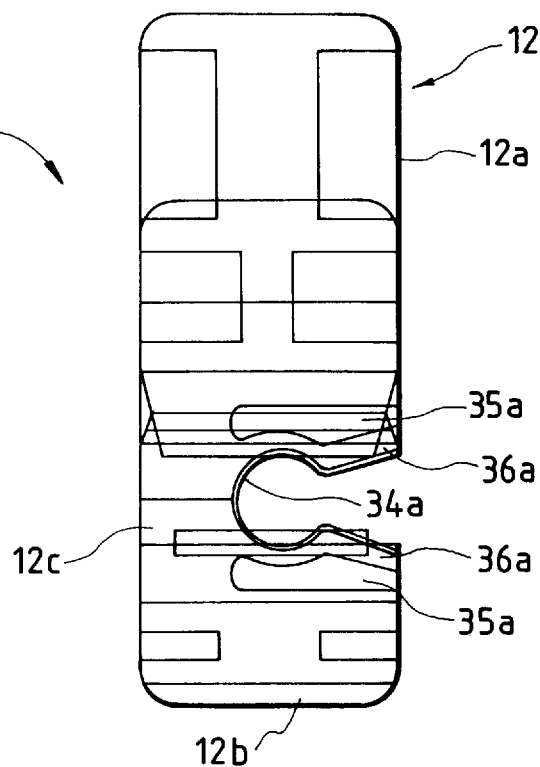
FIG. 16 is a fore end view of the same detaching tool.
Figure 17:
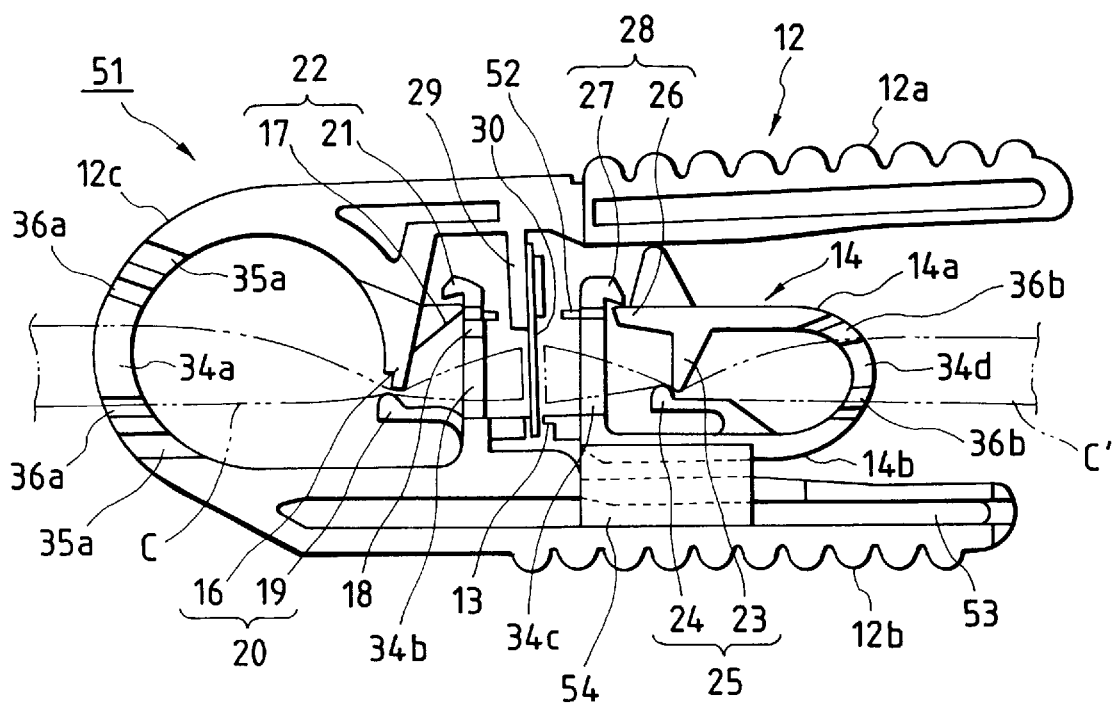
FIG. 17 is a side view showing the same detaching tool when operated.
Figure 18:
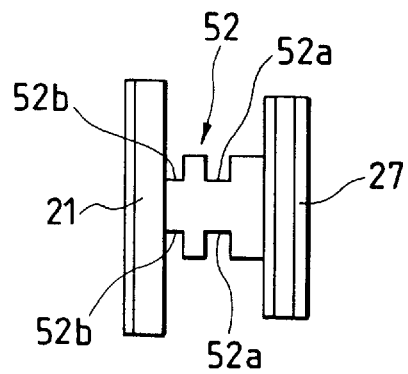
FIG. 18 is a plan view of the stopper of the same detaching tool.
Figure 19A:
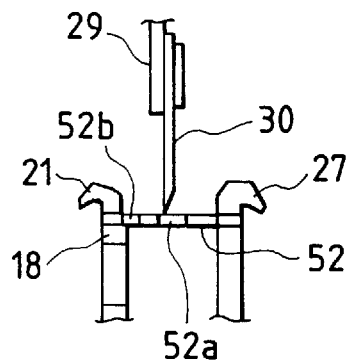
FIGS. 19A, 19B and 19C are illustrations showing the procedure in which in the same detaching tool, the stopper is cut by a cutter.
Figure 19B:
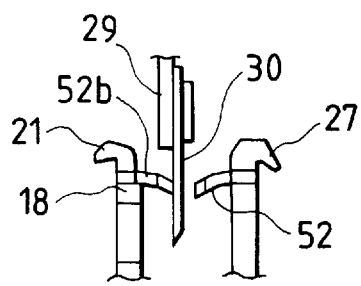
Figure 19C:
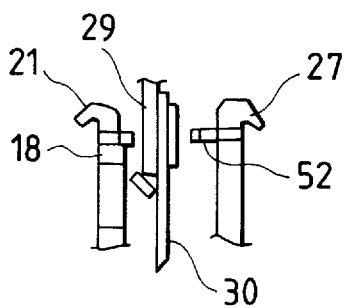
Figure 20:
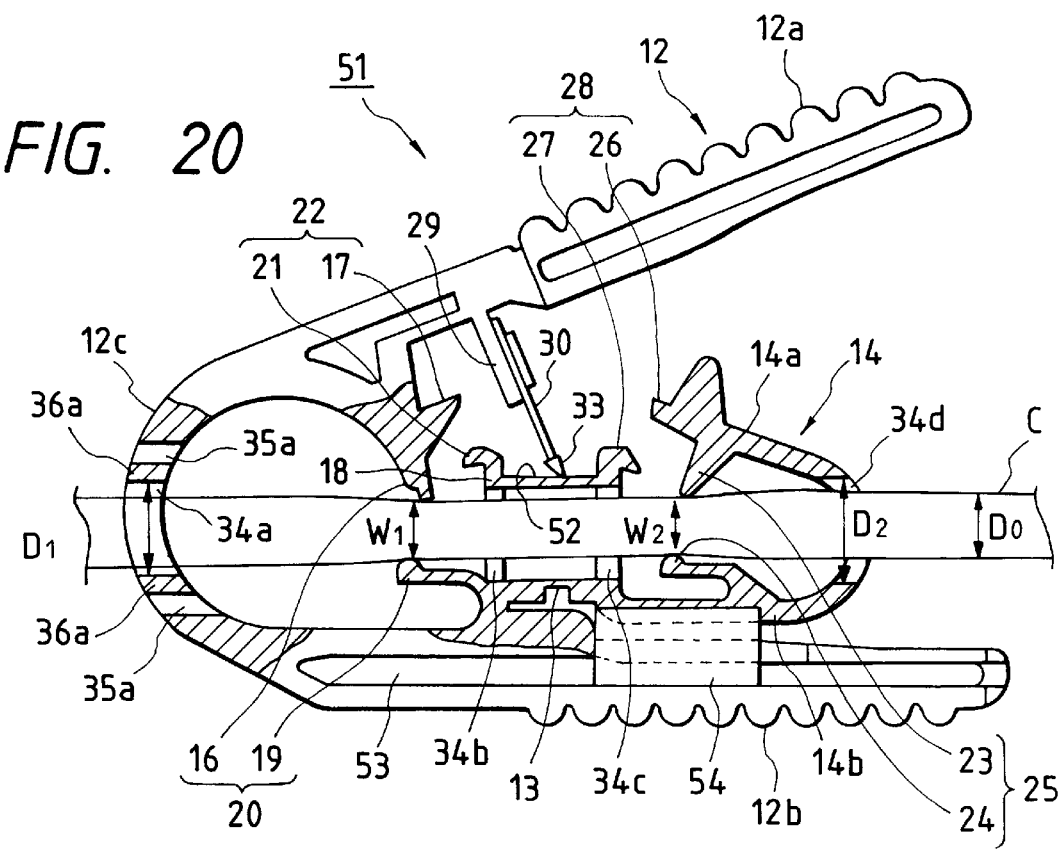
FIG. 20 is a side cross-sectional view showing the state of the same detaching tool before operated.
Figure 21:
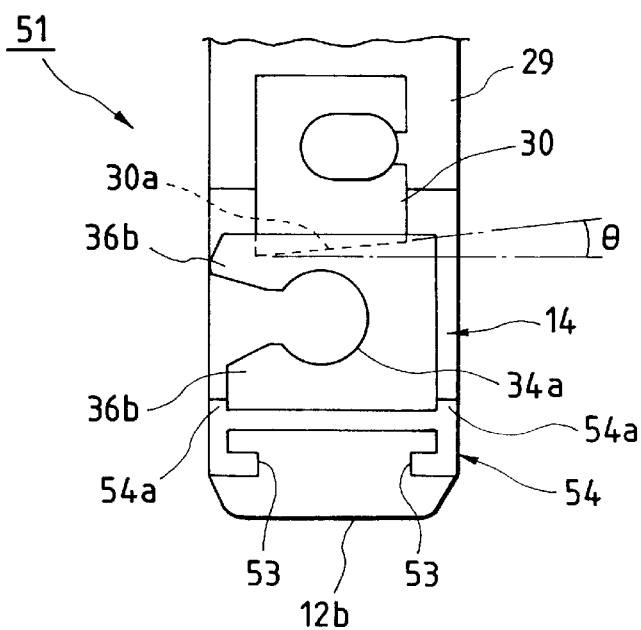
FIG. 21 is an illustration showing the relation between an insertion groove for a tube in the same detaching tool and the cutter.

In FIGS. 14, 15, 16, 17, 18, 19A, 19B, 19C, 20 and 21, there is shown still another embodiment of the detaching tool for a tube for medical treatment according to the present invention. FIG. 14 is a side view showing the state of the detaching tool before operated, FIG. 15 is a rear end view of the detaching tool, FIG. 16 is a fore end view of the detaching tool, FIG. 17 is a side view showing the state of the detaching tool when operated, FIG. 18 is a plan view of a stopper, FIGS. 19A, 19B and 19C are illustrations showing the order in which the stopper is cut by a cutter, FIG. 20 is a side cross-sectional view showing procedure of the detaching tool before operated, and FIG. 21 is an illustration showing the relation between the insertion groove for the tube and the cutter. The same portions as those of the detaching tool for a tube for medical treatment according to the prior art shown in FIGS. 9, 10 and 11 are given the sane reference characters and need not be described.

The detaching tool 51 according to this embodiment has a thin piece-like stopper 52 connecting the protruding piece 18 of the body side grip portion 12 and the other end portion 14b of the separating member 14 together so as to intercept the route in which the cutting edge of the cutter 30 arrives at the tube C. As shown in FIG. 18, this stopper 52 has narrowing grooves 52a and 52b at two locations in the lengthwise direction thereof. By this stopper 52, the cutting edge of the cutter 30 is more reliably prevented from contacting with the tube C during handling such as the mounting of the detaching tool 51 onto the tube C. Also, the separating member 14 is connected to the body 12 for gripping by the thin piece 13 and the stopper 52 and therefore, the separating member 14 can be prevented from coming off during handling.

When as shown in FIGS. 19A, 19B and 19C, the body 12 for gripping is gripped and the cutter 30 is forced in, the stopper 52 is cut by the cutter 30 in the order as shown in FIGS. 19A, 19B and 19C. That is, as shown in FIG. 19A, the cutting edge of the cutter 30 contacts with the stopper 52, and as shown in FIG. 19B, the stopper 52 is cut at the portion of the groove 52a, and as shown in FIG. 19C, the stopper 52 is broken away from the base portion thereof at the portion of the groove 52b by the supporting piece 29 of the cutter 30. Thereby, the stopper 52 is prevented from becoming a hindrance when the cutter 30 is pushed in during the operation of the detaching tool 51.

The stopper 52 may be comprised of a member extending from one of the protruding piece 18 of the body side grip portion 12 or the other end portion 14b of the separating member 14 and not connecting the two together but yet disposed between the two.

In a state in which the grip portions 12a and 12b of the body 12 for gripping kept a little opened, the cutting edge of the cutter 30 on which a protective cover 33 is mounted is urged against and is in contact with the stopper 52 with such a degree of weak force that the cutting edge of the cutter 30 on which the protective cover 33 is mounted does not cut the stopper 52. Thereby, the relative position of the grip portions 12a and 12b is stabilized, and when the detaching tool 51 is operated, the lateral vibration of the cutter 30 is prevented so that the cutting of the tube C by the cutter 30 may be reliably done. This also serves to press the separating member 14 through the stopper 52, and stabilize and hold the separating member 14.

As shown particularly in FIG. 21, one grip portion 12b of the body 12 for gripping is formed with grooves 53 on two sides thereof, and a discrete support member 54 is slidably mounted in these grooves 53. The support member 54 has ribs 54a on the upper surfaces of the two sides thereof, and these ribs 54a abut against the two sides of the separating member 14 in the lower side thereof to thereby prevent the lateral vibration of the separating member 14, thus preventing the separating member 14 from coming off during handling. Also, shock resistance against the falling or the like of the detaching tool 51 can be enhanced. The support member 54 may be comprised of a rib-like projection molded integrally with the body 12 for gripping.

Also, as shown in FIG. 21, the cutting edge 30a of the cutter 30 is made oblique so as to protrude longer toward the opening of the insertion groove 34d (as well as toward the opening of the other insertion groove). In this case, the angle of inclination θ of the cutting edge 30a may preferably be 1° to 30°, and particularly about 3°. If the angle of inclination θ is smaller than 1°, the effect which will be described next will become small, and if the angle of inclination θ is greater than 30°, stroke necessary for cutting will increase or the insertion of the tube will become difficult. By the cutting edge 30a being thus made oblique, the tube C is pushed toward the inner part of the insertion groove 34d when the cutter 30 is pushed in, and therefore the tube C can be prevented from coming off the insertion groove 34d, and the tube C can be reliably captured and cut.

As shown particularly in FIG. 20, in a state in which no gripping force is given to the body 12 for gripping, the spacing $W_1$ or $W_2$ of at least one of the first stream stopping portion 20 and the second stream stopping portion 25 is made smaller than the outer diameter $D_0$ of the tube C to such a degree that when the tube C is held between the two stream stopping portions, the internal flow path thereof is not blockaded. Thereby, when the tube C is inserted into the insertion grooves 34a, 34b, 34c and 34d and passed between the first stream stopping portion 20 and the second stream stopping portion 25, the tube C is pressed and held by at least one of the first stream stopping portion 20 and the second stream stopping portion 25 and therefore, it can be made difficult for the tube C to slip out of the insertion grooves 34a, 34b, 34c and 34d.

If the spacing $W_1$ of the first stream stopping portion 20 of the body 12 for gripping is narrowed, since the pressing force in the first stream stopping portion 20 when the body 12 for gripping is gripped increases to thereby require a larger force, it is preferable to narrow the spacing $W_2$ of the second stream stopping portion 25 of the separating member 14. Also, it is desired that the inner diameters $D_1$ and $D_2$ of the insertion grooves 34a and 34d be made large to a certain degree so that tubes having different outer diameters ($D_0$) can be used as the tube C. Accordingly, specifically it is preferable that $W_2<W_1<D_0<D_1, D_2$ or $W_2<D_0<W_1<D_1, D_2$.

According to this detaching tool 51, upon an emergency condition such as an earthquake, fire, or the like when a patient strongly grips the body 12 for gripping, the cutter 30 cuts the stopper 52, cuts the tube C and further cuts the thin piece 13, thus separating the separating member 14 from the body 12 for gripping, as shown in FIG. 17. Also, the first stream stopping portion 20 presses one of the cut tube C (the tube connected to an artificial kidney device or the like) and stops the blood stream, and the first holding portion 22 comes into engagement therewith and that state is maintained. Also, the second stream stopping portion 25 presses the other cut tube C' (the tube connected to the patient) to stop the blood stream, and the second holding portion 28 comes into engagement therewith to thereby maintain such state. Accordingly, the patient can quickly take shelter while wearing the cut tube C' for medical treatment and the separating member 14 which is acting to close the tube C'.

As has been described above, according to the detaching tool of the present invention for a tube for medical treatment, by being attached to a tube for medical treatment such as artificial dialysis or intravenous drip, the patient can simply grip the body for gripping during a calamity such as an earthquake or a fire to thereby detach the tube for medical treatment and take shelter. Also, provision is made of a stopper for preventing the cutter from arriving at the tube for a gripping force of a predetermined value or less, whereby during handling, the body for gripping can be prevented front being inadvertently closed to thereby operate the detaching tool. Further, when the body for gripping and the separating member are provided with insertion grooves into which the tube for medical treatment can be inserted from sideways to thereby provide a tube inserting portion, it becomes possible to easily mount the detaching device on the tube for medical treatment by one touch after the tube for medical treatment is connected to the patient's body or an artificial kidney device or the like to constitute a dialysis circuit or the like.

As has been described above, by the detaching tool of the present invention for a tube for medical treatment being attached to a tube for artificial dialysis or intravenous drip, the patient becomes able to detach the tube for medical treatment simply by gripping the body for gripping upon a calamity such as an earthquake or a fire and take shelter. Also, by providing the stopper maintaining the body for gripping in its open state, and adapted to be broken away when a gripping force of a predetermined value or greater acts thereon, to thereby enable the body for gripping to be closed, the body for gripping can be prevented from being inadvertently closed to operate the detaching tool.

Also, when in a preferred embodiment of the present invention, insertion grooves into which the tube for medical treatment can be inserted from sideways are formed in the body for gripping and the separating member and are provided as a tube inserting portion, it becomes possible to mount the detaching tool on the tube for medical treatment easily by one touch after the tube for medical treatment is connected to the patient's body or the artificial kidney device or the like to thereby constitute a dialysis circuit or the like.

What is claimed is:

1. A detaching tool for a tube for medical treatment comprising:

a body for gripping which has a bent portion between end portions thereof facing each other and is deformable in an opening-closing direction in the bent portion;

a separating member separably disposed inside said body for gripping, said separating member being adapted to be pressed and closed by said body for gripping when said body for gripping is closed;

a tube inserting portion formed in said body for gripping and said separating member so that a tube for medical treatment may be inserted and held therein;

a first stream stopping portion and a second stream stopping portion provided at a corresponding location inside said body for gripping and a corresponding location inside said separating member so as to press a portion of said tube for medical treatment and stop a stream inside said tube when said body for gripping is closed;

a first holding portion and a second holding portion provided on said body for gripping and said separating member so as to maintain the stream stopping states of said first stream stopping portion and said second stream stopping portion when said body for gripping is closed;

a cutter for cutting said tube for medical treatment including a cutting edge between said first stream stopping portion and said second stream stopping portion when said body for gripping is closed; and a stopper for preventing said cutter from arriving at said tube for a gripping force of a predetermined value or less, wherein said stopper comprises a connecting piece connecting the pair of grip portions of said body for gripping together and preventing said grip portions from being closed, and adapted to be broken away when a gripping force exceeding a predetermined value acts thereon.

2. A detaching tool for a tube for medical treatment according to claim 1, wherein said stopper comprises a thin piece extending from at least one of said body for gripping and said separating member so as to intercept a route in which the cutting edge of said cutter arrives at said tube, and adapted to be cut by said cutter when a gripping force exceeding a predetermined value acts thereon.

3. A detaching tool for a tube for medical treatment according to claim 2, wherein said stopper comprises a thin piece extending in a width direction of the cutting edge of the cutter and a thickness of said thin piece is smaller than a width thereof.

4. A detaching tool for a tube for medical treatment according to claim 2, wherein said thin piece constituting said stopper extends to connect said body for gripping and said separating member together.

5. A detaching tool for a tube for medical treatment according to claim 2, wherein by an initial load when said body for gripping is opened, the cutting edge of said cutter is resiliently urged to contact with said stopper, with such a degree of force that does not cut said thin piece.

6. A detaching tool for a tube for medical treatment according to claim 2, wherein said stopper comprises a cover which is disposed between the cutting edge of the cutter and the tube and is attached to the cutter.

7. A detaching tool for a tube for medical treatment according to claim 1, wherein said stopper comprises a thin piece extending in a width direction of the cutting edge of the cutter and a thickness of said thin piece is smaller than a width thereof.

8. A detaching tool for a tube for medical treatment according to claim 2, further comprising a support member adapted to be inserted into said body for gripping along an axial direction of the tube and to be engaged with said body for gripping, and wherein said support member has a rib for holding said separating member stably in a direction substantially perpendicular to the axial direction of the tube.

9. The detaching tool for a tube for medical treatment according to claim 8 wherein said support member has a projection for holding said separating member stably in a direction substantially perpendicular to the axial direction of the tube.

10. A detaching tool for a tuba for medical treatment according to claim 1, wherein at least one of spacings of said first and second stream stopping portions is made such that said at least one spacing is smaller than an outer diameter of said tube and the internal flow path of the tube is not blockaded in a state in which no gripping force is applied to said body for gripping.

* * * * *